United States Patent [19]
Ottiger

[11] 3,959,379
[45] May 25, 1976

[54] PREPARATION OF PRIMARY AMINES
[75] Inventor: Pius Ottiger, Mount Fern, N.J.
[73] Assignee: Sandoz, Inc., E. Hanover, N.J.
[22] Filed: Aug. 5, 1974
[21] Appl. No.: 494,552

[52] U.S. Cl. .................. 260/584 R; 260/563 C; 260/570.9; 260/583 R; 260/583 H
[51] Int. Cl.$^2$ .......................... C07C 85/06
[58] Field of Search ......... 260/563 C, 570.9, 583 H, 260/583 R, 584 R

[56] References Cited
UNITED STATES PATENTS

| | | | |
|---|---|---|---|
| 3,256,331 | 6/1966 | Jones et al. .................. | 260/583 X |
| 3,347,926 | 10/1967 | Lech ........................... | 260/583 R |
| 3,359,314 | 12/1967 | Brichta et al. ................ | 260/584 X |
| 3,665,037 | 5/1972 | Murakami et al. .............. | 260/563 C |

OTHER PUBLICATIONS

Lloyd, J. Chem. Soc. pp. 822–823 (1965).
Tucker, J. Chem. Educ. Vol. 27, pp. 489–493 (1950).
Chem. Abstracts, Vol. 64, 12540b (1966).
Samné et al., Compt. Rend. Vol. 249, No. 22, pp. 2340–2341 (1959).

Primary Examiner—Helen M. S. Sneed
Attorney, Agent, or Firm—Gerald D. Sharkin; Richard E. Vila; Frederick H. Weinfeldt

[57] ABSTRACT

Primary aliphatic amines are prepared by reacting a corresponding aliphatic oxime with hydrazine in the presence of Raney nickel.

17 Claims, No Drawings

PREPARATION OF PRIMARY AMINES

This invention relates to a chemical process, and more particularly to a process for the conversion of aliphatic oximes to primary aliphatic amines, to the preparation of intermediates useful in said process, and to such intermediates.

An embodiment of this invention is the preparation of primary amines of the formula I:

$$R-CH_2-NH_2 \quad (I)$$

wherein R is
A. an alkyl radical having from 1 to 7 carbon atoms, which may be unsubstituted or substituted by one or two members independently selected from the group consisting of hydroxy, phenyl, or cyclohexyl;
B. an alkenyl or alkadienyl radical having from 1 to 7 carbon atoms;
C. a cycloaliphatic radical having from 5 to 8 ring carbon atoms which may be saturated or mono-ethylenically unsaturated, and may be unsubstituted or substituted by from 1 to 3 lower alkyls, which may be like or unlike; or
D. phenyl, which may be unsubstituted or substituted by one or two members independently selected from the group consisting of phenyl, chloro and lower alkyl;
which comprises reacting an oxime of the formula II:

$$R-CH=NOH \quad (II)$$

wherein R is as defined,
with hydrazine in the presence of Raney nickel in a suitable medium, i.e. process a).

In the above-presented definitions, the term lower alkyl is understood to indicate alkyl having from 1 to 4 carbon atoms, i.e. methyl, ethyl, propyl and butyl, including isomeric forms where such exist, but are preferably unbranched and more preferably methyl.

Alkyl, alkenyl and alkadienyl radicals suitable as R may be branched or unbranched, but are preferably unbranched. Preferred alkyl radicals are those having from 3 to 5 carbon atoms, and a ω-hydroxy substituent. Preferred cycloaliphatic radicals are those having from 5 to 6 ring-carbon atoms which are saturated and are unsubstituted or mono-substituted. Preferred phenyl radicals are those which are unsubstituted or mono-substituted.

The compounds I are generally well known and useful as chemical intermediates, e.g. in the preparation of pharmaceutical compounds, surface active agents, anti-static agents, emulsifiers, and anti-oxidants.

The above-described amines, i.e. Compounds I, e.g. 5-amino-1-pentanol, are customarily prepared from Compounds II by high pressure hydrogenation techniques. This invention advantageously obviates the use of high pressure hydrogen, which requires specialized equipment and is inherently dangerous and inconvenient.

In process (a), suitable reaction medium is an alkanol having from 1 to 4 carbon atoms, i.e. methanol, ethanol, propanol, or butanol, including their isomeric forms where such exist (process a). In the selection of the medium to be employed in process (a), it is preferable that compounds II be at least partially soluble in the medium, and more preferably that a medium be selected in which the compound II used, is completely soluble. Process a) is carried out at about atmospheric pressure, at moderate temperatures, e.g. from about 40° to 120°C., preferably at from about 60° to 85°C., such as the reflux temperature of the reaction mixture when wet ethanol is used as the reaction medium. As water is not deleterious to the reaction, hydrazine may conveniently be employed in the form of hydrazine hydrate, and the medium need not be moisture-free. Reaction time is not critical and is typically from about 1 to 10 hours. The amine products (I) may be recovered from the reaction mixture and purified by conventional techniques, e.g. fractional distillation, crystallization or chromatographic techniques.

Raney nickel is a finely divided nickel-aluminum alloy commonly suspended in water (as a safety precaution, as the alloy is pyrophoric in air), which is obtainable commerically. Raney nickels suitable for use in process a) are well known and typically contain nickel and aluminum in varying weight ratios, e.g. in a weight ratio of from about 25:75 to 75:25, preferably about 40:60 to 60:40, and more preferably about 1:1. A preferred form of Raney nickel is Raney nickel No. 28* which is a granular nickel-aluminum alloy having a weight ratio of 1:1, in water. The Raney nickel need be present in process a) in amounts of from about 1.0 to 50%, preferably from about 5 to 20%, by weight based on the weight of the compounds II. The hydrazine is preferably present in a molar excess, e.g. in a molar ratio of at least about 1.2:1, usually in a ratio of from about 1.5 to 15:1 of hydrazine to the oxime, preferably in a molar ratio of from about 2 to 4:1.

*obtainable from W. R. Grace Co.

The oximes, i.e. compounds of the formula II, employed as starting material in preparation of compounds I are either known per se or may be prepared from known materials by available procedures. The oximes (II) may be prepared in the conventional manner for the preparation of oximes, such as the known methods for the conversion of an aldehyde to an oxime. For example, Compounds II may be prepared from corresponding aldehydes, i.e. compounds of the formula

$$R-\overset{\overset{\displaystyle O}{\|}}{C}H \quad III$$

wherein R is as defined above,
by treatment with a hydroxylamine salt, e.g. the hydrochloride, in an acidic aqueous medium, e.g. dilute hydrochloric acid (process b).

The compounds of the formula III employed as starting material in the preparation of the compounds II are either known per se or may be prepared from known materials by available procedures.

Compounds II, as well as intermediates in the preparation thereof, may be recovered from reaction mixtures and refined by conventional means, e.g. by crystallization, fractional distillation and chromatographic techniques.

A particular embodiment of this invention is the preparation of 5-amino-1-pentanol (a compound I) by treating the corresponding oxime, i.e. 5-oximino-1-pentanol (a coumpound II), by the applying of the method of this invention (process a'). 5-Amino-1-pentanol is a known compound and is useful as a chemical intermediate e.g. as disclosed in U.S. Pat. No. 3,637,699, and also in the photographic field.

The oxime used in process (a') may be obtained by process (b'), i.e. reacting 5-hydroxy-n-pentaldehyde with hydroxylamine hydrochloride in an aqueous acidic medium, e.g. dilute hydrochloric acid, at moderate temperatures, e.g. at from about 40° to 80°C., preferably at from about 55° to 70°C. Reaction time is typically from about 10 minutes to 2 hours. The oxime, 5-oximino-1-pentanol, is soluble in the reaction mixture of process (b'), but may be recovered from the reaction mixture and purified by conventional means. Since the oxime is a crystalline solid it may conveniently be recovered, e.g. by "springing", i.e. by basicifying the reaction mixture and isolating the oxime by cooling so that it precipitates; or "salting out", i.e. by neutralizing the reaction mixture, saturating with a highly soluble salt such as sodium chloride, and then extracting the oxime with an inert organic solvent, such as ethyl acetate. The isolated oxime may be refined by recrystallizing, e.g. from ethyl acetate or petroleum ether. The preferred solvent for process (a') is ethanol.

Another embodiment of this invention is the preparation of 5-hydroxy-n-pentaldehyde used in process (b') by cleaving dihydropyran (process c) with dilute aqueous hydrochloric acid, e.g. from 3 to 30% by weight, e.g. 5 to 10%, preferably 2N hydrochloric acid, at moderate temperatures, e.g. from about 45° to 65°C., preferably about 55°C. Process (c) generally only requires from about ¼ to 1 hour.

Process (b') may be carried out directly on the reaction mixture resulting from process (c), as the acidic conditions and water present in such mixture are not deleterious to process (b') and actually may conveniently serve as the reaction medium for process (b').

The preparation of 5-amino-1-pentanol by the above-described methods can be conveniently represented by Reaction Scheme A which follows:

REACTION SCHEME A

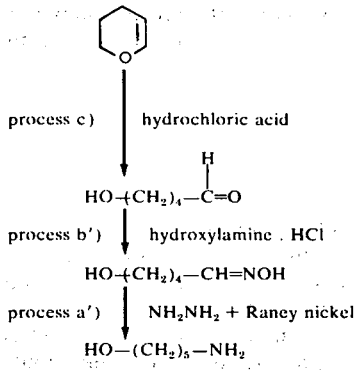

process c) | hydrochloric acid

HO—(CH₂)₄—C=O
            |
            H process b') | hydroxylamine . HCl

HO—(CH₂)₄—CH=NOH process a') | NH₂NH₂ + Raney nickel

HO—(CH₂)₅—NH₂

The following examples are provided as illustrative of the invention; all temperatures are Centigrade and room temperature is 20° to 30°C. unless indicated otherwise.

EXAMPLE 1

5-Amino-1-pentanol

HO—(CH₂)₅—NH₂

Step A: Preparation of 5-oximino-1-pentanol*
HO—(CH₂)₄—CH=NOH
*may also be known as 5-hydroxypentaldehyde oxime, 5-oximo-1-pentanol, 5-hydroxyimino-1-pentanol, 5-oximido-1-pentanol or ω-oximino-n-pentanol.

A 5 liter flask equipped with a mechanical stirrer is charged with 795 ml. of aqueous 2 Normal hydrochloric acid and heated to 55°C. The heat source is removed and 409 g. of dihydropyran (4.85 mole) is added dropwise through an addition funnel at such a rate that the reaction temperature is maintained at 60° to 65°C., but not exceeding 65°C. Total addition time is about 30 minutes and a clear orange solution results. 390 g. of hydroxylamine hydrochloride is then added portionwise over 15 minutes and the temperature is allowed to drop during the addition. The final reaction mixture is allowed to cool to room temperature.

The reaction mixture is then made distinctly basic by dropwise addition of 400 ml. of 50% sodium hydroxide aqueous solution with ice/water bath cooling at 25°-35°C. Cooling of the reaction mixture to 0° to −5°C. with ice/methanol bath cooling results in an off-white precipitate which drops out of solution. This precipitate is filtered and then washed with copious amounts of petroleum ether and sucked dry under vacuum to obtain crude 5-oximino-1-pentanol, i.e. the oxime product.

A second crop of crude oxime product is obtained by saturating the aqueous mother liquor with sodium chloride and extracting four times with 1 liter portions of warm (about 40°C.) ethyl acetate. The organic extracts are combined and dried over anhydrous sodium sulfate. The solvents are evaporated in vacuum and the crude oxime product is crystallized from petroleum ether. The product is then filtered and washed with petroleum ether and sucked dry to obtain a second crop of the oxime product.

The crude oxime fractions are combined and recrystallized from warm ethyl acetate with a charcoal treatment to yield refined 5-oximino-1-pentanol as white needles, m.p. 85°-89°C.

Step B: Preparation of 5-amino-1-pentanol

In a 12 liter flask having a reflux condenser, under nitrogen atmosphere is mixed together at room temperature 585 g. of 5-oximino-1-pentanol, 585 ml. of hydrazine (hydrate), and 5.85 liters of ethanol. This forms a clear yellow solution which is heated to 50°C. The heat source and reflux condenser are then removed.

89 g. of Raney nickel (No. 28) active catalyst in water is added portionwise to the reaction mixture over a period of 3 hours. The addition is carried out very cautiously to avoid excess foaming action. The reaction is exothermic and self-sustaining at reflux temperature. The addition of Raney nickel is stopped when addition no longer envokes foaming action. 200 g. of hydrazine (hydrate) is then added very cautiously to the reaction mixture through a dropping funnel over 1 hour and the reaction mixture refluxed over night (about 16 hours). The reaction mixture is cooled to room temperature and solids removed by filtering over diatomaceous earth (celite). The filtrate (clear yellow) is evaporated on a rotary evaporator to remove solvent. The resulting oil is then distilled under high vacuum yielding refined 5-amino-1-pentanol (b.p. at 0.4 mm Hg., 66° to 69°C).

EXAMPLE 2

Repeating the procedure of step B of Example 1, using in place of the 5-oximino-1-pentanol, used therein, an approximately equivalent amount of:
 a. the oxime of n-octaldehyde;
 b. the oxime of benzaldehyde;
 c. the oxime of n-hex-3-enaldehyde;
 d. the oxime of 5-phenylpentaldehyde; and
 e. the oxime of 4-methylcyclohexaldehyde;
there is similarly obtained:
 a. n-octylamine;
 b. benzylamine;

c. n-hex-3-enylamine;
d. 5-phenylpentylamine; and
e. 4-methylcyclohexylmethylamine.

What is claimed is:

1. A process for the preparation of a primary amine of the formula $$R-CH_2-NH_2$$

wherein R is
- A. an alkyl radical having from 1 to 7 carbon atoms, which may be unsubstituted or substituted by one or two members independently selected from the group consisting of hydroxy, phenyl, or cyclohexyl;
- B. an alkenyl or alkadienyl radical having from 1 to 7 carbon atoms;
- C. a cycloaliphatic radical having from 5 to 8 ring carbon atoms which may be saturated or mono-ethylenically unsaturated, and may be unsubstituted or substituted by from 1 to 3 lower alkyls, which may be like or unlike; or
- D. phenyl, which may be unsubstituted or substituted by one or two members independently selected from the group consisting of phenyl, chloro and lower alkyl;

which comprises reacting an oxime of the formula $$R-CH=NOH$$

wherein R is as defined, with hydrazine in the presence of a catalytic amount of Raney nickel having from about 25 to 75 parts by weight of nickel and from about 75 to 25 parts by weight aluminum in finely-divided form, in an alkanol having from 1 to 4 carbon atoms, at a temperature of from about 40° to 120°C., at about atmospheric pressure, and recovering the resulting primary amine.

2. A method of claim 1 in which the alkanol is ethanol.

3. A method of claim 1 in which the Raney nickel has a parts by weight ratio of nickel to aluminum of from about 40:60 to 60:40.

4. A method of claim 3 in which the temperature is from about 60° to 85°C.

5. A method of claim 4 in which the molecular ratio of the hydrazine to oxime is from about 1.5 to 15:1.

6. A method of claim 5 in which the molecular ratio of the hydrazine to oxime is from about 2 to 4:1.

7. A method of claim 5 in which the Raney nickel is present in an amount of from about 1.0 to 50% by weight based on the weight of the oxime.

8. A method of claim 7 in which the Raney nickel is present in an amount of from about 5 to 20% by weight based on the weight of the oxime.

9. A method of claim 7 in which the Raney nickel has a parts by weight ratio of nickel to aluminum of about 1:1.

10. A method of claim 1 in which R is of type (A).

11. A method of claim 1 in which R is of type (B).

12. A method of claim 1 in which R is of type (C).

13. A method of claim 1 in which R is of type (D).

14. A method of claim 9 in which R is 5-hydroxypentyl.

15. A method of claim 10 in which R is 5-hydroxypentyl.

16. A method of claim 15 in which the alkanol is ethanol.

17. A method of claim 10 in which R is an alkyl radical having from 3 to 5 carbon atoms and an ω-hydroxy group.

* * * * *

UNITED STATES PATENT OFFICE
CERTIFICATE OF CORRECTION

Patent No. 3,959,379      Dated May 25, 1976

Inventor(s) Pius Ottiger

It is certified that error appears in the above-identified patent and that said Letters Patent are hereby corrected as shown below:

Column 5, line 21, remove the word "lower" and after the word "alkyls," add -- having from 1 to 4 carbon atoms --;

line 26, remove the word "lower" and after the word "alkyl" add -- having from 1 to 4 carbon atoms --;

line 35, after the word "weight", insert the word -- of --.

Column 6, lines 27 & 28, "5-hydroxypentyl" should read -- 4-hydroxybutyl --; lines 29 & 30, "5-hydroxypentyl" should read -- 4-hydroxybutyl --.

*Signed and Sealed this*

*ninth* Day of *August 1977*

[SEAL]

*Attest:*

RUTH C. MASON
*Attesting Officer*

C. MARSHALL DANN
*Commissioner of Patents and Trademarks*